US00PP18791P2

(12) United States Plant Patent
Bradford

(10) Patent No.: US PP18,791 P2
(45) Date of Patent: May 6, 2008

(54) PEACH TREE NAMED 'ROSE PRINCESS'

(50) Latin Name: *Prunus persica*
Varietal Denomination: Rose Princess

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,909

(22) Filed: Dec. 13, 2006

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP7,070 P 12/1989 Bradford
PP7,507 P 4/1991 Bradford

*Primary Examiner*—Kent Bell

(57) ABSTRACT

The present invention relates to a new and distinct variety of peach tree, *Prunus persica,* broadly characterized by a medium size, vigorous, hardy, self-fertile, productive and regular bearing tree. The fruit matures under the ecological conditions described in late May, with first picking on May 29, 2006. The fruit is uniformly large in size, acidic and sweet in flavor, globose to oblate in shape, clingstone in type, firm and non-melting in texture, yellow in flesh color, and mostly red in skin color.

1 Drawing Sheet

Botanical classification: *Prunus persica.*
Variety denomination: 'Rose Princess'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Rose Princess'.

During the spring of 1996 I gathered fruit from an unpatented peach tree in my experimental orchard located near Le Grand, Calif., in Merced County (San Joaquin Valley) that had been designated as "5P57". This particular peach tree was itself a first generation cross using 'Spring Bright' (U.S. Plant Pat. No. 7,507) yellow flesh nectarine as the selected seed parent and an unnamed yellow flesh peach (unpatented) as the selected pollen parent. The seeds from this fruit were removed, cracked, stratified, germinated, and grown as seedlings on their own root in my greenhouse as a group labeled "5P57 (OP)". Upon reaching dormancy that fall they were transplanted to a cultivated area in the experimental orchard described above. During the fruit evaluation season of 1999 I selected the claimed variety as a single tree from this group of "5P57 (OP)" described above. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed grandparent, 'Spring Bright' (U.S. Plant Pat. No. 7,507) nectarine by being productive, requiring medium chilling requirements, and by producing fruit that is nearly globose in shape, acidic and sweet in flavor, yellow in flesh color, and almost full red in skin color, but is quite distinct by producing peaches, instead of nectarines, that are non-melting in flesh texture and that ripen about thirty days earlier.

The present variety is most similar to 'Crown Princess' (U.S. Plant Pat. No. 7,070) peach by producing peaches that are very firm and non-melting in texture, yellow in flesh color, and mostly red in skin color, but is distinguished therefrom by having reniform instead of globose glands, by being more productive, by requiring less chilling hours, and by producing fruit that tastes better and that matures about twelve days earlier.

SUMMARY OF VARIETY

In summary, the present variety is characterized by a medium size, vigorous, hardy, self-fertile, productive and regular bearing tree. The fruit matures under the ecological conditions described in late May, with first picking on May 29, 2006. The fruit is uniformly large in size, acidic and sweet in flavor, globose to oblate in shape, clingstone in type, firm and non-melting in texture, yellow in flesh color, and mostly red in skin color.

DRAWING

The accompanying photograph consists of four whole fruits positioned to display the characteristics of the skin color and form, one fruit divided transversely to the suture plane to reveal the flesh and stone, a freshly cleaned stone, two insets to reveal buds and a blossom, and a typical tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 1, 2006, on the original tree during its tenth growing season. All major color code designations are by reference to the Inter-Society Color Council, National Bureau of Standards. Common color names are also used occasionally.

Parentage

Parentage: An open pollinated seedling of '5P57' (Unpatented) Peach.

Tree

Size: Medium, reaching and maintaining a height of 11' [3.35 m.] and a spread of 12' [3.66 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and open.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 525 hours.

Trunk:

*Size.*—Medium, reaching a maximum diameter of 6" [152 mm.] after the tenth growing season.

*Texture.*—Shaggy.

*Bark color.*—A Brownish gray [64. brGy] and Deep brown [56. deep Br] variegation.

*Lenticels.*—Approximate Number Per Square Inch: 8. Color: Light yellowish brown [76. l.yBr]. Typical Size: ⅛" [3.2 mm.] to 7/16" [11.1 mm.]. Shape: Eye-shaped to elongated.

Branches:

*Size.*—Diameter of limb is 3¾" [95 mm.] measured 12" above the crotch, 2½" [64 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 60 on second year wood. Color: Light orange yellow [70. l.OY]. Typical Size: 1/64" [0.4 mm.] to 3/32" [2.4 mm.] on second year wood. Shape: Elongated.

Leaves:

*Size.*—Large. Average Length: 6¼" [159 mm.]. Average width: 1 9/16" [40 mm.].

*Arrangement.*—Alternate.

*Thickness.*—Medium.

*Form.*—Elliptical.

*Apex.*—Acuminate.

*Base.*—Acute, with a base angle of 75 to 85 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. lYG].

*Petiole.*—Average Length: ¼" [6.4 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Brilliant yellow green [116. brill.YG] becoming Moderate reddish brown [43. m.rBr] with maturity.

*Glands.*—Number: 2 to 4 per leaf. Position: Alternately positioned on petiole and base of blade. Size: Large. Form: Reniform. Color: Brilliant yellow green [116. brill.YG] becoming Light olive brown [94. l.OlBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, large.

*Average flower diameter.*—1⅞" [47.6 mm.].

*Number of petals.*—Usually five, extra petal fragments commonly occur, double blossoms rarely observed.

*Petal shape.*—Circular to oval.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Dark reddish orange [38. d.rO] over a Light yellow [86. l.Y] center at bloom onset.

*Stigma color.*—Light greenish yellow [101. l.gY].

*Sepal color.*—Dark purplish red [259. d.pR].

*Sepal length.*—¼" [7 mm.].

*Sepal width.*—3/16" [5 mm.].

*Average pistil length.*—13/16" [20.6 mm.].

*Average stamen length.*—⅝" [15.9 mm.].

*Fragrance.*—Moderate.

*Blooming period.*—Medium, a few days before 'Spring Bright' (U.S. Plant Pat. No. 7,507) nectarine.

*Onset of bloom.*—One percent on Feb. 20, 2006.

*Date of full bloom.*—Mar. 6, 2006.

*Duration of bloom.*—One to two weeks, dependent on ambient temperature.

*Number per cluster.*—1 to 3 with single flowers most common.

FRUIT

Maturity when described: Firm ripe, Jun. 1, 2006.

Date of first picking: May 29, 2006.

Date of last picking: Jun. 8, 2006.
Size: Uniform, large.
*Average diameter axially.*—2⅞" [73 mm.].
*Average diameter across suture plane.*—3⅛" [79 mm.].
*Average diameter across cheek plane.*—3⅛" [79 mm.].
*Typical weight.*—7.9 ounces [224 grams].
Form: Uniform, oblate.
*Longitudinal section form.*—Oblate.
*Axial view.*—Round.
Suture: A shallow groove extending from the base, along the side and just past the pistil point, sharper in the stem cavity and toward the apex, Pale yellow [89. p.Y] stitching within the groove.
Ventral surface: Rounded, lightly lipped throughout.
Lips: Fairly equal.
Cavity: Flaring, elongated in the suture plane, suture showing on both sides, Brilliant yellow [83. brill.Y] stem markings typical.
*Depth.*—7/16" [11.1 mm.].
*Breadth.*—1⅛" [28.6 mm.].
Base: Truncate.
Apex: Rounded to truncate, somewhat cordate if viewed parallel to suture.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Moderate.
*Tendency to crack.*—Somewhat in wet season.
*Color.*—Dark red [16. d.R] mottled over a Moderate reddish orange [37. m.rO] background with slight Yellowish white [92. yWhite] freckling on the sides.
Down: Moderate, does not roll up when rubbed.
Flesh:
*Color.*—Brilliant yellow [83. brill.Y] acquiring Strong red [12. s.R] flecking with increasing maturity.
*Surface of pit cavity.*—Light yellow [86. l.Y] broken fibers when twisted from stone.
*Amygdalin.*—Moderate.
*Juice.*—Abundant, rich.
*Texture.*—Firm, non-melting.
*Fibers.*—Abundant, fine.
*Ripens.*—Earlier toward the apex.
*Flavor.*—Acidic and sweet, typically 13 to 15 brix.
*Aroma.*—Moderate.
*Eating quality.*—Very good.

STONE

Type: Clingstone.
Form: Oval.
Hilum: Narrow.
Base: Oblique.
Apex: Obtuse with an average angle of 110 degrees.
Sides: Equal.
Surface: Irregularly furrowed toward the apex and ventral edge, randomly pitted throughout.
Ridges: Jagged.
External color: Light yellowish brown [76. l.yBr].
Pit wall color when cracked: Pale orange yellow [73. p.OY].
Cavity surface color: Light orange yellow [70. l.OY].
Average pit wall thickness: ¼" [6.4 mm.].
Average width: 1" [25.4 mm.].
Average length: 1⅜" [34.9 mm.].
Average breadth: 13/16" [20.6 mm.].
Tendency to split: Slight.
Kernel:
*Form.*—Oval.
*Skin color.*—Pale yellow [89. p.Y] when first removed.
*Pellicle color.*—Light olive brown [94. l.OlBr].
*Vein color.*—Light yellow [86. l.Y].
*Taste.*—Bitter.
*Viable.*—Only by utilizing embryo rescue techniques.
*Average width.*—½" [12.7 mm.].
*Average length.*—¾" [19.1 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Crown Princess' (U.S. Plant Pat. No. 7,070) peach by producing peaches that are very firm and non-melting in texture, yellow in flesh color, and mostly red in skin color, but is distinguished therefrom by having reniform instead of globose glands, by being more productive, by requiring less chilling hours, and by producing fruit that tastes better and that matures about twelve days earlier.

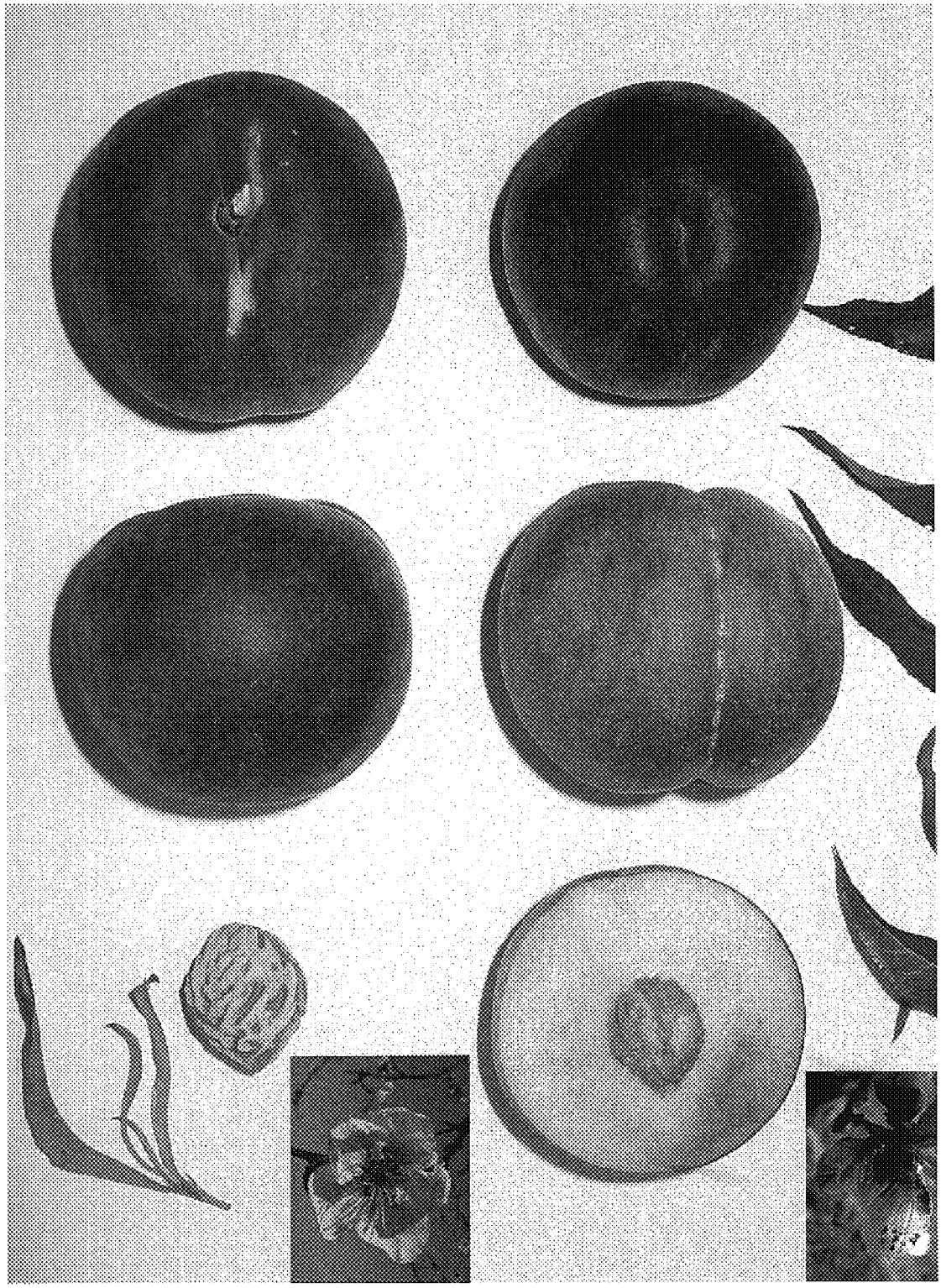

* * * * *